United States Patent
Zeng et al.

(10) Patent No.: US 11,644,415 B2
(45) Date of Patent: May 9, 2023

(54) SYSTEM FOR MEASURING GAS TEMPERATURE AND COMPONENT CONCENTRATIONS IN COMBUSTION FIELD BASED ON OPTICAL COMB

(71) Applicants: Chongqing Institute of East China Normal University, Chongqing (CN); ROI Optoelectronics Technology CO, LTD., Shanghai (CN); East China Normal University, Shanghai (CN); University of Shanghai for Science and Technology, Shanghai (CN)

(72) Inventors: Heping Zeng, Chongqing (CN); Kangwen Yang, Chongqing (CN); Hai Li, Chongqing (CN)

(73) Assignees: CHONGQING INSTITUTE OF EAST CHINA NORMAL UNIVERSITY, Chongqing (CN); ROI OPTOELECTRONICS TECHNOLOGY CO, LTD., Shanghai (CN); EAST CHINA NORMAL UNIVERSITY, Shanghai (CN); UNIVERSITY OF SHANGHAI FOR SCIENCE AND TECHNOLOGY, Shanghai (CN)

(*) Notice: Subject to any disclaimer, the term of this patent is extended or adjusted under 35 U.S.C. 154(b) by 241 days.

(21) Appl. No.: 17/177,672

(22) Filed: Feb. 17, 2021

(65) Prior Publication Data
US 2021/0255095 A1 Aug. 19, 2021

(30) Foreign Application Priority Data
Feb. 18, 2020 (CN) .......................... 202010098143.6

(51) Int. Cl.
*G01N 21/31* (2006.01)
*G01J 5/58* (2022.01)
*G01N 33/00* (2006.01)

(52) U.S. Cl.
CPC ................ *G01N 21/31* (2013.01); *G01J 5/58* (2013.01); *G01N 33/0027* (2013.01); *G01N 2201/06113* (2013.01)

(58) Field of Classification Search
CPC .............. G01N 21/31; G01N 33/0027; G01N 2201/06113; G01J 5/58
See application file for complete search history.

(56) References Cited

FOREIGN PATENT DOCUMENTS

| CN | 112284566 | * | 1/2021 | ............. G01K 11/32 |
| WO | WO-2016034511 A | * | 3/2016 | ................ G01J 3/10 |

* cited by examiner

Primary Examiner — Catherine T. Rastovski
(74) Attorney, Agent, or Firm — Hodgson Russ LLP (57) ABSTRACT

Provided is a system for measuring gas temperature and component concentrations in a combustion field based on optical comb. The system includes two pulse laser devices, two continuous laser devices, a beam splitting device, a measurement path, an interference signal detecting device, an optical processing and electrical processing device and a signal acquisition and analysis device. The measurement path refers to the combustion field to be measured. The interference signal detecting device outputs an interference signal. The optical processing and electrical processing device includes several optic elements and electrical elements, and outputs an adaptive compensation signal and an asynchronous sampling clock signal after a series of processing on output of the two pulse laser devices and two continuous laser devices. The signal acquisition and analysis device outputs the measurement result based on the adaptive compensation signal, the asynchronous sampling clock signal and a stable interference signal.

11 Claims, 4 Drawing Sheets

SYSTEM FOR MEASURING GAS TEMPERATURE AND COMPONENT CONCENTRATIONS IN COMBUSTION FIELD BASED ON OPTICAL COMB

CROSS-REFERENCE TO RELATED APPLICATIONS

This application claims priority to Chinese Patent Application Serial No. 202010098143.6, filed on Feb. 18, 2020, the entire disclosure of which is incorporated by reference herein.

FIELD

The present disclosure relates to a non-contact optical measurement technology field, and more particularly to a system for measuring gas temperature and component concentrations in a combustion field based on optical comb.

BACKGROUND

In recent years, parameter measurement of a combustion field has always been an important research topic, which can directly provide an important basis for the study of combustion mechanism, combustion efficiency and emission reduction of environmental pollutants. Therefore, the accurate analysis of the state of the combustion field is of vital importance to industrial production and scientific research.

The temperature and component concentrations of combustion gas are the most important parameters to understand the combustion state, and they are key indexes to characterize the combustion intensity and heat release efficiency. At present, traditional contact temperature measurement technologies have disadvantages of slow reaction speed, interference to combustion flow field, short service life of equipment and so on. Moreover, these devices cannot last long in hot and complex combustion environments.

Laser-based combustion diagnosis technology, as a real-time and non-contact measurement method, can realize rapid and non-interference measurement of combustion parameters. At present, Tunable Diode Laser Absorption Spectroscopy (TDLAS) is the most commonly used among many Laser-based combustion diagnosis techniques. TDLAS system has advantages of compact structure, fast response speed and strong environmental adaptability, which can accurately reflect the combustion temperature and component concentrations in the combustion process in real time. However, the output wavelength of the existing tunable diode laser has a certain tuning range, but the wavelength scanning range is very narrow, usually only a few wave numbers, which limits the selection of absorption component and the determination of target absorption line, and cannot meet the simultaneous online measurement of combustion gas temperature and concentrations of various components. Therefore, how to provide a method or system that can simultaneously measure the gas temperature and the concentrations of various components in the combustion field online has become the inevitable demand for high precision and rapid diagnosis in the combustion field.

SUMMARY

Embodiments of the present disclosure provide a system for measuring gas temperature and component concentrations in a combustion field based on optical comb. The system includes a first pulse laser device, a second pulse laser device, a first continuous laser device, a second continuous laser device, a beam splitting device, a coupler, a photodetector, an optical processing and electrical processing device, a mixer, and a signal acquisition and analysis device.

The first pulse laser device includes a first output port and a second output port, and is configured to output a first pulse laser beam via the first output port and the second output port respectively.

The second pulse laser device includes a third output port and a fourth output port, and is configured to output a second pulse laser beam via the third output port and the fourth output port respectively. A waveband of each of the first pulse laser beam and the second pulse laser beam covers an absorption line range of components in gas to be measured.

The first continuous laser device is configured to generate a first laser output. The second continuous laser device is configured to generate a second laser output.

The coupler is coupled to the third output port and an output of the combustion field, and is configured to generate an optical beat signal by processing the second pulse laser beam and the third pulse laser beam.

The photodetector is configured to convert the optical beat signal to an electric signal.

The optical processing and electrical processing device is coupled to the second output port, the fourth output port, the first continuous laser, and the second continuous laser respectively, and configured to generate an adaptive compensation signal and an asynchronous sampling clock signal by performing optical processing and electrical processing on the first laser output, the second laser output, the first pulse laser beam, and the second pulse laser beam.

The mixer is configured to receive the electric signal and the adaptive compensation signal, and to generate a mixed signal based on the electric signal and the adaptive compensation signal.

The signal acquisition and analysis device is configured to collect the mixed signal by using the asynchronous sampling clock signal as a trigger clock to obtain a stable time domain interference signal, and to obtain the gas temperature and the component concentrations through processing based on the time domain interference signal.

EMBODIMENTS OF THE PRESENT DISCLOSURE

The present disclosure will be further described in detail below with reference to the accompanying drawings and embodiments. Same or similar reference numbers throughout the specification indicate same or similar elements or element having same or similar functions. It should be understood that the specific embodiments described herein are only used to explain the present disclosure, and should not be understood as limitation to the present disclosure.

Figure 1:
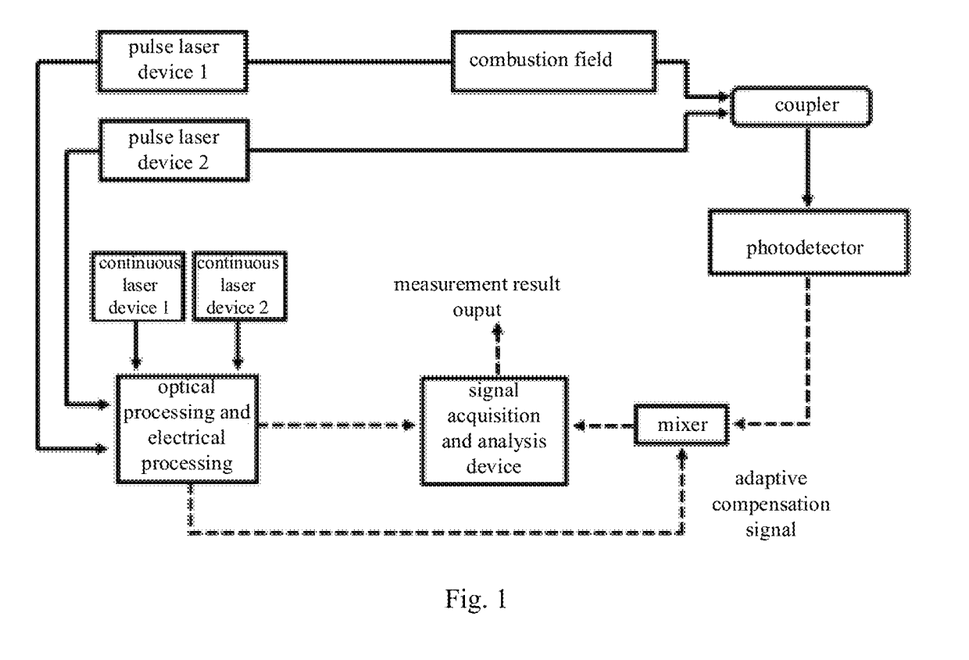
FIG. 1 is a schematic diagram illustrating a system for measuring gas temperature and component concentrations in a combustion field based on optical comb according to an embodiment of the present disclosure.

Referring to FIG. 1, the system for measuring gas temperature and component concentrations in a combustion field based on optical comb according to the present disclosure includes a laser source device, a beam splitting device, an interference signal detecting device, an optical processing and electrical processing device, a mixer and a signal acquisition and analysis device.

The laser source device includes two pulse laser devices and two continuous laser devices. A first pulse laser device includes a first output port and a second output port, and is configured to output a first pulse laser beam via the first output port and the second output port respectively. A second pulse laser device includes a third output port and a fourth output port, and is configured to output a second pulse laser beam via the third output port and the fourth output port respectively. A waveband of each of the first pulse laser beam and the second pulse laser beam covers an absorption line range of components in gas to be measured. A first continuous laser device is configured to generate a first laser output. A second continuous laser device is configured to generate a second laser output.

A center wavelength of an output spectrum of each of the first pulse laser device and the second pulse laser device is 1550 nm, a center wavelength of an output spectrum of the first continuous laser device is 1550 nm, and a center wavelength of an output spectrum of the second continuous laser device is 1564 nm.

The beam splitting device is coupled to the first output port and configured to split the first pulse laser beam into multiple laser pulses of different wavebands. The multiple laser pulses of different wavebands are to be absorbed by the components in the combustion field whose absorption spectrums are corresponding to the wavebands of the multiple laser pulses, to generate a third pulse laser beam.

The interference signal detecting device realizes the coherent detecting of two pulse laser beams to output an interference signal. The interference signal detecting device includes a coupler and a photodetector. The coupler is coupled to the third output port and an output of the combustion field, and configured to generate an optical beat signal by processing the second pulse laser beam and the third pulse laser beam. The photodetector is configured to convert the optical beat signal to an electric signal.

The optical processing and electrical processing device is coupled to the second output port, the fourth output port, the first continuous laser device, and the second continuous laser device respectively, and configured to generate an adaptive compensation signal and an asynchronous sampling clock signal by performing optical processing and electrical processing on the first laser output, the second laser output, the first pulse laser beam, and the second pulse laser beam.

Before the first pulse laser beam and the second pulse laser beam enter into the optical processing and electrical processing device, an output spectrum of the first pulse laser device and an output spectrum of the second pulse laser device are broadened to an extra wide spectrum coverage of 1-1.7 μm.

The mixer is configured to receive the electric signal and the adaptive compensation signal, and to generate a mixed signal based on the electric signal and the adaptive compensation signal.

The interference signal outputted by the interference signal detecting device is mixed with the adaptive compensation signal, to eliminate relative carrier envelope phase offset jitter.

The signal acquisition and analysis device is configured to collect the mixed signal by using the asynchronous sampling clock signal as a trigger clock to obtain a stable time domain interference signal, and to obtain the gas temperature and the component concentrations through processing based on the time domain interference signal. The mixed signal is further processed by the signal acquisition and analysis device to eliminate relative repetition frequency jitter.

Since the spectrum coverage of the laser source device is relatively wider, hundreds of absorption lines may be realized through a single scanning, and absorption spectra information is rich. Therefore, one or more target absorption lines may be selected according to the selection principle, and finally according to the principle of double or multiple line temperature measurement, the temperature measurement result is obtained, which greatly improves the accuracy of measurement result.

In detail, the signal acquisition and analysis device includes a data acquisition card and a computer. The data acquisition card is configured to obtain the stable interference signal. The computer is configured to: perform fast Fourier transform on the time domain interference signal to obtain an absorption spectral signal of a component to be measured; perform baseline fitting, background subtraction and peak integral processing on the absorption spectral signal to obtain an integral absorbance of an absorption line; obtain the gas temperature based on a ratio of intensities of two absorption lines of a same component; and obtain the component concentration of the component through an inversion method based on the integral absorbance of any absorption line.

Beer-Lambert's Law states that, after passing through the area of the gas to be measured, the laser with the frequency of v is absorbed by the gas to be measured, the integral absorbance of the gas may be represented as:

$$A = \int_{-\infty}^{\infty} A_v(v) dv = \int_{-\infty}^{\infty} -\ln\left(\frac{I_o}{I}\right) dv = P \cdot X \cdot S(T) \cdot L,$$

where, $A_v$ is an absorbance of the gas, I is laser intensity before passing through the combustion field, $I_0$ is laser intensity after passing through the combustion field, P is a pressure of the gas, X is a mole fraction of the component, T is the gas temperature, L is a transmission length of the first pulse laser beam in the combustion field, and S(T) is the intensity of the absorption line at the temperature T.

S(T) is only related with the temperature, and may be calculated as follows:

$$S(T) = S(T_0) \frac{T_0}{T} \frac{Q(T_0)}{Q(T)} \exp\left[-\frac{hcE''}{K}\left(\frac{1}{T} - \frac{1}{T_0}\right)\right] \times \frac{\left[1 - \exp\left(-\frac{hcv_i}{KT}\right)\right]}{\left[1 - \exp\left(-\frac{hcv_i}{KT_0}\right)\right]},$$

where, $T_0$ is a reference temperature, Q(T) represents a partition function of a target component, h is a Planck constant, k is a Boltzmann constant, c is a laser speed, E" is a low-state energy level value, and $v_i$ is a center frequency of the absorption line.

In the double line temperature measurement, two absorption lines of a same target component are determined, the partition function is get rid of the ratio of intensities of two absorption lines to obtain the ratio as:

$$R = \frac{A_1}{A_2} = \frac{S_1(T)}{S_2(T)} = \frac{S_1(T_0)}{S_2(T_0)} \times \exp\left[-\frac{hc}{k}(E_1'' - E_2'')\left(\frac{1}{T} - \frac{1}{T_0}\right)\right],$$

where, $A_1$ and $A_2$ are the integral absorbances corresponding to the two absorption lines respectively, $E_1''$ and $E_2''$ are the low-state energy level values corresponding to the two absorption lines respectively, $S_1(T)$ and $S_2(T)$ are the intensities of the two absorption lines at the temperature T respectively, and $S_1(T_0)$ and $S_2(T_0)$ are the intensities of the two absorption lines at the reference temperature $T_0$ respectively.

Thus, the gas temperature may be determined as:

$$T = \frac{\frac{hc(E_2'' - E_1'')}{k}}{\ln\frac{A_1}{A_2} + \ln\frac{S_2(To)}{S_1(T_0)} + \frac{hc}{k}\frac{(E_2'' - E_1'')}{T_0}}.$$

Based on the above equations, the temperature of the combustion field may be measured by calculating the ratio R of the integral absorbances of the two absorption lines. After calculating the temperature T, the mol fraction X of the component may be calculated by selecting one spectral line:

$$X = \frac{A}{P. \ S(T). \ L}.$$

Figure 2:
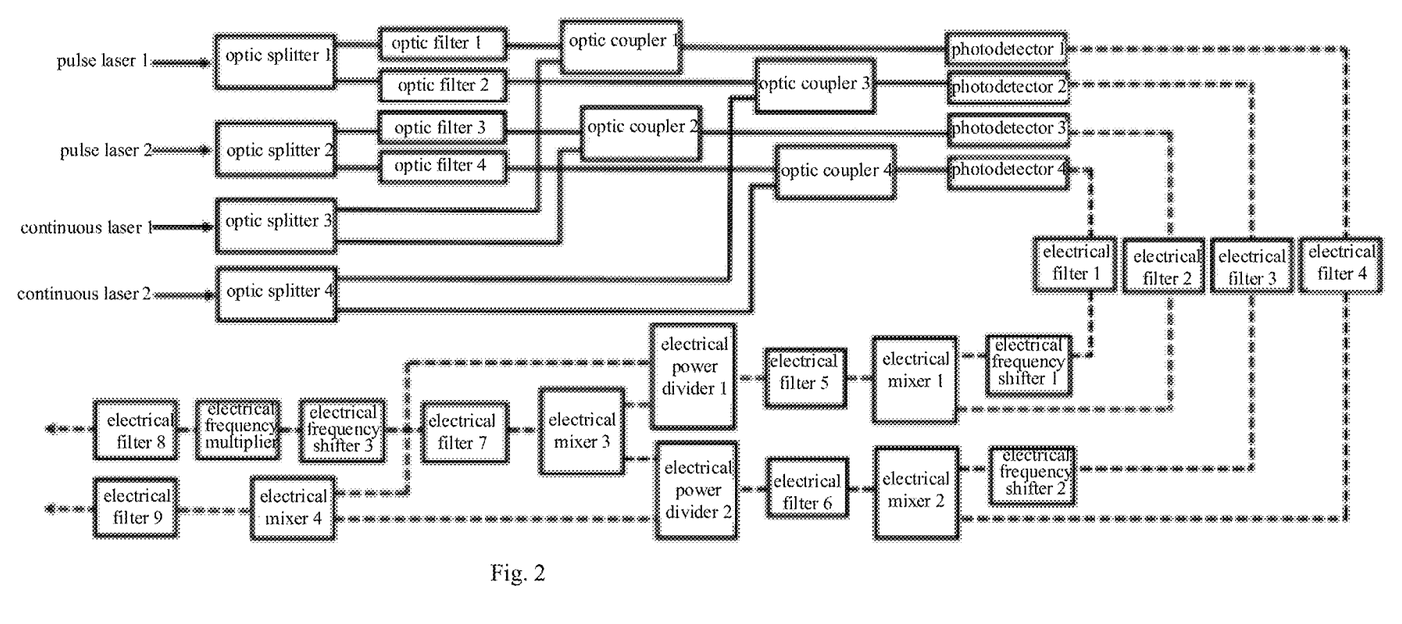
FIG. 2 is a schematic diagram of an optical processing and electrical processing device according to an embodiment of the present disclosure.

Referring to FIG. 2, the optical processing and electrical processing device may include a first optic splitter, a second optic splitter, a third optic splitter, a fourth optic splitter, a first optic coupler, a second optic coupler, a third optic coupler, a fourth optic coupler, a first optic filter, a second optic filter, a third optic filter, a fourth optic filter, a first photodetector, a second photodetector, a third photodetector, a fourth photodetector, a first electrical filter, a second electrical filter, a third electrical filter, a fourth electrical filter, a fifth electrical filter, a sixth electrical filter, a seventh electrical filter, an eighth electrical filter, a ninth electrical filter, a first electrical frequency shifter, a second electrical frequency shifter, a third electrical frequency shifter, a first electrical mixer, a second electrical mixer, a third electrical mixer, a fourth electrical mixer, a first electrical power divider, a second electrical power divider, and an electrical frequency multiplier.

The first pulse laser beam and the second pulse laser beam are split by the first optic splitter and the second optic splitter respectively to generate multiple pulse laser. Spectral filtering is performed on the multiple pulse laser respectively by the first optic filter, the second optic filter, the third optic filter, and the fourth optic filter. The first laser output is split by the third optic splitter to generate two laser beams, and the second laser output is split by the fourth optic splitter to generate two laser beams. One laser beam outputted by the third optic splitter and an output laser of the first optic filter are input into the first optic coupler for processing to output a first optical beat signal, and the other laser beam outputted by the third optic splitter and an output laser of the third optic filter are input into the second optic coupler for processing to output a second optical beat signal. One laser beam outputted by the fourth optic splitter and an output laser of the second optic filter are input into the third optic coupler for processing to output a third optical beat signal, and the other laser beam outputted by the fourth optic splitter and an output laser of the fourth optic filter are input into the fourth optic coupler for processing to output a fourth optical beat signal. The first optical beat signal, the second optical beat signal, the third optical beat signal, and the fourth optical beat signal are converted by the first photodetector, the second photodetector, the third photodetector and the fourth photodetector respectively to generate a first electrical signal, a second electrical signal, a third electrical signal and a fourth electrical signal. The first electrical signal, the second electrical signal, the third electrical signal and the fourth electrical signal are filtered respectively by the first electrical filter, the second electrical filter, the third electrical filter and the fourth electrical filter. An output signal of the first electrical filter is inputted into the first electrical frequency shifter for frequency shift, and an output signal of the first electrical frequency shifter is inputted into the first electrical mixer together with an output signal of the second electrical filter for frequency mixing. An output signal of the third electrical filter is inputted into the second electrical frequency shifter for frequency shift, and an output signal of the second electrical frequency shifter is inputted into the second electrical mixer together with an output signal of the fourth electrical filter for frequency mixing. An output signal of the first electrical mixer and an output signal of the second electrical mixer are filtered by the fifth electrical filter and the sixth electrical filter respectively, and then inputted into the first electrical power divider and the second electrical power divider. A signal inputted into the first electrical power divider is divided into two signals, in which one signal is inputted into the third electrical mixer, and the other signal is inputted into the fourth electrical mixer. A signal inputted into the second electrical power divider is divided into two signals, in which one signal is inputted into the third electrical mixer, and the other signal is inputted into the fourth electrical mixer. An output signal of the third electrical mixer is filtered by the seventh electrical filter, and then inputted into the third electrical frequency shifter for frequency shift, and then inputted into the electrical frequency multiplier. An output signal of the electrical frequency multiplier is filtered by the eighth electrical filter to generate the asynchronous sampling clock signal, and an output signal of the fourth electrical mixer is filtered by the ninth electrical filter to generate the adaptive compensation signal.

In an embodiment, the components in the gas to be measured include one or more of $H_2O$, $CO_2$, and CO.

In the following, two example embodiments are illustrated to further explain the system of the present disclosure.

Embodiment 1

Figure 5:
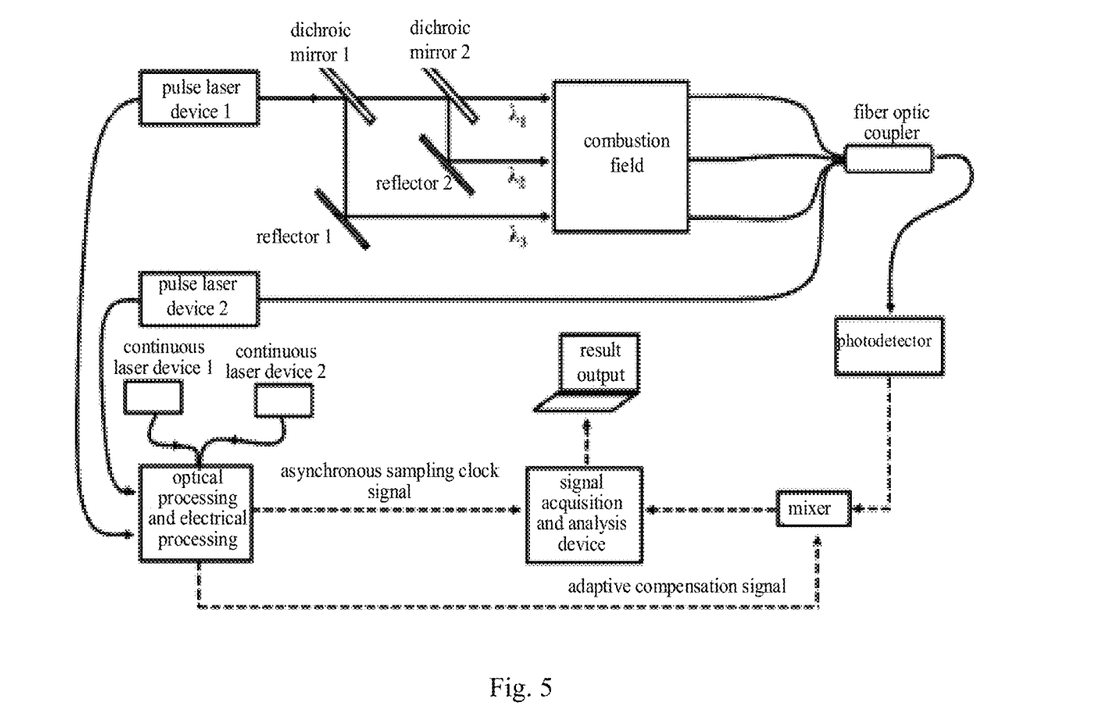
FIG. 5 is a schematic diagram of a system for measuring gas temperature and component concentrations in a combustion field based on optical comb according to a first embodiment.

Referring to FIG. 5, in combustion field analysis, parameter measurement of a certain target component can be satisfied, and parameters of different target components (corresponding to different bands, such as $H_2O$, $CO_2$, CO, etc.) can be measured simultaneously through cascading optical filters of different bands.

The system includes a laser source device, an optical filtering device, a measurement path, an interference signal detecting device, an optical processing and electrical processing device, and a signal acquisition and analysis device. The optical filtering device mainly includes optical filters (dichroic mirrors) and reflectors, which split the pulse laser beam into multiple laser pulses of different bands $\lambda_1$, $\lambda_2$, $\lambda_3$. The measurement path mainly includes the combustion field to be measured. With respect to further details, reference may be made to above description and FIGS. 3-4.

Figure 3:
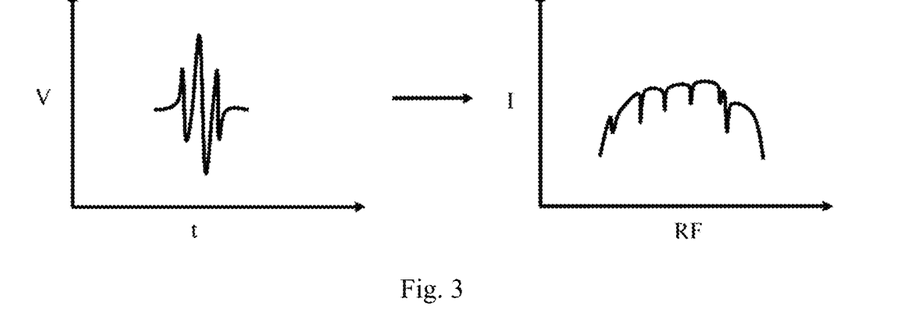
FIG. 3 is a schematic diagram illustrating a fast Fourier transform process of a time domain interference signal according to an embodiment of the present disclosure.
Figure 4:
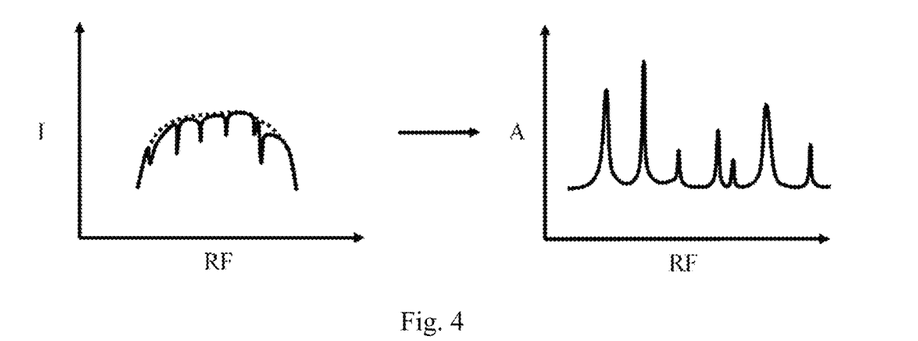
FIG. 4 is a schematic diagram of a further processing of a RF spectral signal according to an embodiment of the present disclosure.

Referring to FIG. 3, the left figure represents the time-domain interference signal detected and collected, where the abscissa is time t and the ordinate is signal strength V. The figure on the right represents the RF spectral signal obtained after Fourier transform processing of the time-domain interference signal. The abscissa represents RF, and the ordinate represents signal strength I. After baseline fitting, background subtraction, peak integration and other processing on the absorption spectral signal, the integral absorbance of absorption line is obtained. See FIG. 4 for the specific process. The left figure represents the baseline fitting process of the RF spectral signal, where the abscissa is RF and the ordinate is signal strength I. The figure on the right shows the process of background subtraction and peak integration of the RF spectral signal, where the abscissa represents RF, and the ordinate represents absorbance A. Finally, the combustion field temperature and inversion of the component concentration is realized according to the principle of double-line or multi-line temperature measurement, and the measurement results of corresponding parameters are output through the computer display.

Embodiment 2

Figure 6:
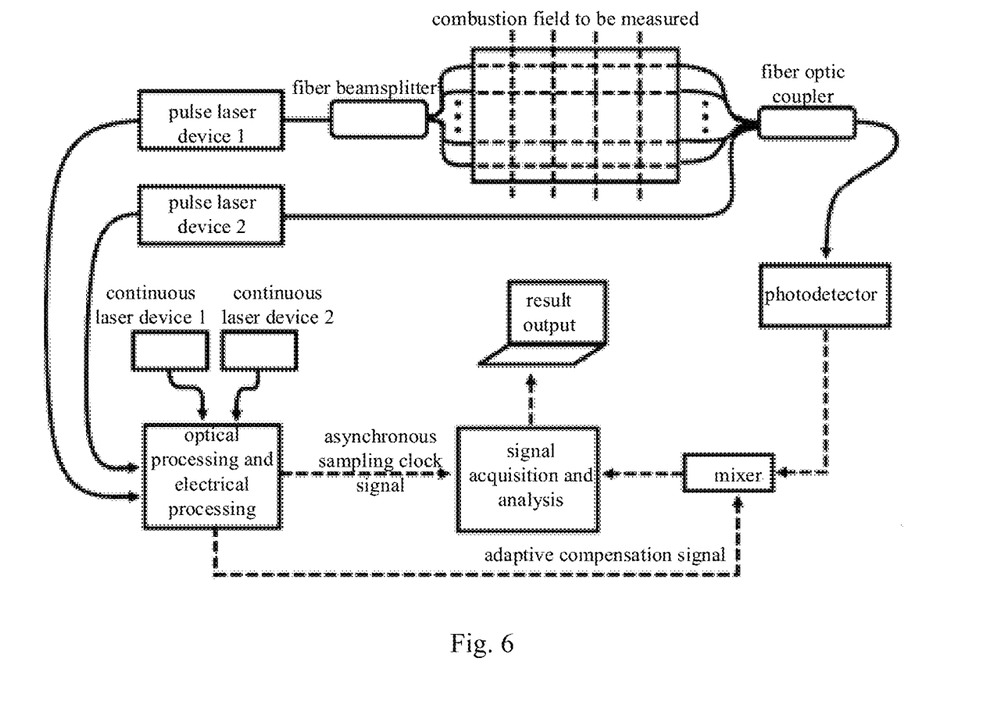
FIG. 6 is a schematic diagram of a system for measuring gas temperature and component concentrations in a combustion field based on optical comb according to a second embodiment.

Referring to FIG. 6, in this embodiment, the two-dimensional flow field reconstruction in the combustion field to be measured may be realized through cascading optic splitters.

The difference between Embodiment 1 and Embodiment 2 is that, the laser beam output from the right port of the first pulse laser device is inputted into the optical splitting device, in which the optical splitting device consists of an optical splitter. The optical splitter performs equal power splitting on the single laser beam to form a multi-path simultaneous measurement system. For other details, reference may also be made to above description.

Although explanatory embodiments have been shown and described, it would be understood that above embodiments are exemplary, and shall not be understood as limitation to the present disclosure, and it would be appreciated by those skilled in the art that changes, alternatives, and modifications may be made in the embodiments within the scope of the disclosure.

What is claimed is:

1. A system for measuring gas temperature and component concentrations in a combustion field based on optical comb, comprising:
    a first pulse laser device, comprising a first output port and a second output port, and configured to output a first pulse laser beam via the first output port and the second output port respectively, wherein a waveband of the first pulse laser beam covers an absorption line range of components in gas to be measured;
    a second pulse laser device, comprising a third output port and a fourth output port, and configured to output a second pulse laser beam via the third output port and the fourth output port respectively, wherein a waveband of the second pulse laser beam covers the absorption line range of components in gas to be measured;
    a first continuous laser device, configured to generate a first laser output;
    a second continuous laser device, configured to generate a second laser output;
    a beam splitting device, coupled to the first output port and configured to split the first pulse laser beam into multiple laser pulses of different wavebands, wherein the multiple laser pulses of different wavebands are to be absorbed by the components in the combustion field whose absorption spectrums are corresponding to the wavebands of the multiple laser pulses, to generate a third pulse laser beam;
    a coupler, coupled to the third output port and an output of the combustion field, and configured to generate an optical beat signal by processing the second pulse laser beam and the third pulse laser beam;
    a photodetector, configured to convert the optical beat signal to an electric signal;
    an optical processing and electrical processing device, coupled to the second output port, the fourth output port, the first continuous laser device, and the second continuous laser device respectively, and configured to generate an adaptive compensation signal and an asynchronous sampling clock signal by performing optical processing and electrical processing on the first laser output, the second laser output, the first pulse laser beam, and the second pulse laser beam;
    a mixer, configured to receive the electric signal and the adaptive compensation signal, and to generate a mixed signal based on the electric signal and the adaptive compensation signal; and
    a signal acquisition and analysis device, configured to collect the mixed signal by using the asynchronous sampling clock signal as a trigger clock to obtain a stable time domain interference signal, and to obtain the gas temperature and the component concentrations through processing based on the time domain interference signal.

2. The system of claim 1, wherein the signal acquisition and analysis device comprises:
    a data acquisition card, configured to collect the mixed signal by using the asynchronous sampling clock signal as the trigger clock to obtain the stable time domain interference signal; and
    a computer, configured to:
        perform fast Fourier transform on the time domain interference signal to obtain an absorption spectral signal of a component to be measured;
        perform baseline fitting, background subtraction and peak integral processing on the absorption spectral signal to obtain an integral absorbance of an absorption line;
        obtain the gas temperature based on a ratio of intensities of two absorption lines of a same component; and
        obtain the component concentration of the component through an inversion method based on the integral absorbance of any absorption line.

3. The system of claim 2, wherein the computer is configured to obtain the integral absorbance according to a formula of:

$$A = \int_{-\infty}^{\infty} A_v(v) dv = \int_{-\infty}^{\infty} -\ln\left(\frac{I_o}{I}\right) dv = P \cdot X \cdot S(T) \cdot L$$

where, v is a frequency of the first pulse laser beam, $A_v$ is an absorbance of the gas, I is laser intensity before passing through the combustion field, $I_0$ is laser intensity after passing through the combustion field, P is a pressure of the gas, X is a mole fraction of the component, T is the gas temperature, L is a transmission length of the first pulse laser beam in the combustion field, and S(T) is the intensity of the absorption line at the temperature T.

4. The system of claim 3, wherein the computer is configured to calculate S(T) according to a formula of:

$$S(T) = S(T_0) \frac{T_0}{T} \frac{Q(T_0)}{Q(T)} \exp\left[-\frac{hcE''}{K}\left(\frac{1}{T} - \frac{1}{T_0}\right)\right] \times \frac{\left[1 - \exp\left(-\frac{hcv_i}{KT}\right)\right]}{\left[1 - \exp\left(-\frac{hcv_i}{KT_0}\right)\right]}$$

where, $T_0$ is a reference temperature, Q(T) represents a partition function of a target component, h is a Planck constant, k is a Boltzmann constant, c is a laser speed, E" is a low-state energy level value, and $v_i$ is a center frequency of the absorption line.

5. The system of claim 4, wherein the computer is configured to obtain the ratio of intensities of two absorption lines of a same component according to a formula of:

$$R = \frac{A_1}{A_2} = \frac{S_1(T)}{S_2(T)} = \frac{S_1(T_0)}{S_2(T_0)} \times \exp\left[-\frac{hc}{k}(E_1'' - E_2'')\left(\frac{1}{T} - \frac{1}{T_0}\right)\right],$$

where, $A_1$ and $A_2$ are the integral absorbances corresponding to the two absorption lines respectively, $E_1''$ and $E_2''$ are the low-state energy level values corresponding to the two absorption lines respectively, $S_1(T)$ and $S_2(T)$ are the intensities of the two absorption lines at the temperature T respectively, and $S_1(T_0)$ and $S_2(T_0)$ are the intensities of the two absorption lines at the reference temperature $T_0$ respectively.

6. The system of claim 5, wherein the computer is configured to obtain the gas temperature according to a formula of:

$$T = \frac{\frac{hc(E_2'' - E_1'')}{k}}{\ln\frac{A_1}{A_2} + \ln\frac{S_2(T_0)}{S_1(T_0)} + \frac{hc}{k}\frac{(E_2'' - E_1'')}{T_0}}.$$

7. The system of claim 6, wherein the computer is configured to obtain the component concentration of the component according to a formula of:

$$X = \frac{A}{P.\ S(T).\ L}.$$

8. The system of claim 1, wherein the components in the gas to be measured comprise one or more of $H_2O$, $CO_2$, and CO.

9. The system of claim 1, wherein the optical processing and electrical processing device comprises a first optic splitter, a second optic splitter, a third optic splitter, a fourth optic splitter, a first optic coupler, a second optic coupler, a third optic coupler, a fourth optic coupler, a first optic filter, a second optic filter, a third optic filter, a fourth optic filter, a first photodetector, a second photodetector, a third photodetector, a fourth photodetector, a first electrical filter, a second electrical filter, a third electrical filter, a fourth electrical filter, a fifth electrical filter, a sixth electrical filter, a seventh electrical filter, an eighth electrical filter, a ninth electrical filter, a first electrical frequency shifter, a second electrical frequency shifter, a third electrical frequency shifter, a first electrical mixer, a second electrical mixer, a third electrical mixer, a fourth electrical mixer, a first electrical power divider, a second electrical power divider, and an electrical frequency multiplier, wherein, the first pulse laser beam and the second pulse laser beam are split by the first optic splitter and the second optic splitter respectively to generate multiple pulse laser;

spectral filtering is performed on the multiple pulse laser respectively by the first optic filter, the second optic filter, the third optic filter, and the fourth optic filter;

the first laser output is split by the third optic splitter to generate two laser beams, and the second laser output is split by the fourth optic splitter to generate two laser beams;

one laser beam outputted by the third optic splitter and an output laser of the first optic filter are input into the first optic coupler for processing to output a first optical beat signal;

the other laser beam outputted by the third optic splitter and an output laser of the third optic filter are input into the second optic coupler for processing to output a second optical beat signal;

one laser beam outputted by the fourth optic splitter and an output laser of the second optic filter are input into the third optic coupler for processing to output a third optical beat signal;

the other laser beam outputted by the fourth optic splitter and an output laser of the fourth optic filter are input into the fourth optic coupler for processing to output a fourth optical beat signal;

the first optical beat signal, the second optical beat signal, the third optical beat signal, and the fourth optical beat signal are converted by the first photodetector, the second photodetector, the third photodetector and the fourth photodetector respectively to generate a first electrical signal, a second electrical signal, a third electrical signal and a fourth electrical signal;

the first electrical signal, the second electrical signal, the third electrical signal and the fourth electrical signal are filtered respectively by the first electrical filter, the second electrical filter, the third electrical filter and the fourth electrical filter;

an output signal of the first electrical filter is inputted into the first electrical frequency shifter for frequency shift, and an output signal of the first electrical frequency shifter is inputted into the first electrical mixer together with an output signal of the second electrical filter for frequency mixing;

an output signal of the third electrical filter is inputted into the second electrical frequency shifter for frequency shift, and an output signal of the second electrical frequency shifter is inputted into the second electrical mixer together with an output signal of the fourth electrical filter for frequency mixing;

an output signal of the first electrical mixer and an output signal of the second electrical mixer are filtered by the fifth electrical filter and the sixth electrical filter respectively, and then inputted into the first electrical power divider and the second electrical power divider;

a signal inputted into the first electrical power divider is divided into two signals, in which one signal is inputted into the third electrical mixer, and the other signal is inputted into the fourth electrical mixer;

a signal inputted into the second electrical power divider is divided into two signals, in which one signal is inputted into the third electrical mixer, and the other signal is inputted into the fourth electrical mixer;

an output signal of the third electrical mixer is filtered by the seventh electrical filter, and then inputted into the third electrical frequency shifter for frequency shift, and then inputted into the electrical frequency multiplier;

an output signal of the electrical frequency multiplier is filtered by the eighth electrical filter to generate the asynchronous sampling clock signal; and an output signal of the fourth electrical mixer is filtered by the ninth electrical filter to generate the adaptive compensation signal.

10. The system of claim 1, wherein an output spectrum of the first pulse laser device and an output spectrum of the second pulse laser device are broadened to an extra wide spectrum coverage of 1-1.7 μm.

11. The system of claim 1, wherein a center wavelength of an output spectrum of each of the first pulse laser device and the second pulse laser device is 1550 nm, a center wavelength of an output spectrum of the first continuous laser device is 1550 nm, and a center wavelength of an output spectrum of the second continuous laser device is 1564 nm.

* * * * *